(12) United States Patent
De-Heyder et al.

(10) Patent No.: US 8,624,004 B2
(45) Date of Patent: Jan. 7, 2014

(54) PURIFICATION OF HBV ANTIGENS FOR USE IN VACCINES

(75) Inventors: Koen De-Heyder, Rixensart (BE); Peter Schu, Rixensart (BE); Michelle Serantoni, Rixensart (BE); Omer Van-Opstal, Rixensart (BE)

(73) Assignee: Glaxosmithkline Biologicals, S.A., Rixensart (BE)

( * ) Notice: Subject to any disclaimer, the term of this patent is extended or adjusted under 35 U.S.C. 154(b) by 641 days.

(21) Appl. No.: 12/342,220

(22) Filed: Dec. 23, 2008

(65) Prior Publication Data
US 2009/0123496 A1    May 14, 2009

Related U.S. Application Data

(63) Continuation of application No. 10/344,211, filed as application No. PCT/EP01/09100 on Aug. 7, 2001, now abandoned.

(30) Foreign Application Priority Data

Aug. 10, 2000 (GB) .................................. 0019728.5
Jan. 18, 2001 (GB) .................................. 0101334.1

(51) Int. Cl.
*C12P 21/02* (2006.01)
*C12N 15/00* (2006.01)

(52) U.S. Cl.
USPC .......................... 530/412; 530/413; 424/227.1

(58) Field of Classification Search
None
See application file for complete search history.

(56) References Cited

U.S. PATENT DOCUMENTS

| | | | |
|---|---|---|---|
| 4,649,192 A | 3/1987 | Van Wijnendaele et al. | |
| 4,683,294 A | 7/1987 | Van Wijnendaele et al. | |
| 4,720,385 A | 1/1988 | Lembach | 424/176.1 |
| 5,242,812 A | 9/1993 | Even-Chen | 435/70.3 |
| 5,340,575 A | 8/1994 | Eibl et al. | 424/196.11 |
| 6,362,320 B1 | 3/2002 | Park et al. | 530/412 |

FOREIGN PATENT DOCUMENTS

| | | |
|---|---|---|
| CA | 1272457 | 8/1990 |
| EP | 0130 619 | 2/1985 |
| EP | 0339667 | 2/1989 |
| EP | 314 240 | 5/1989 |
| EP | 0314240 | 5/1989 |
| EP | 0510996 | 10/1992 |
| EP | 0533 492 A2 | 3/1993 |
| GB | 1030777 | 5/1966 |
| WO | WO9211291 | 7/1992 |
| WO | WO 96/12802 | 5/1996 |
| WO | WO9945957 | 9/1999 |
| WO | WO 00/37104 | 6/2000 |

OTHER PUBLICATIONS 2-mercaptoethanol published in Chemxper.com.
Dressman et al. J. Virol. 1975, vol. 16, No. 3, pp. 508-515.
Structure published in DTT.html.
Choi, et al., "Expression of Hepatitis B virus surface antigen gene in *E. coli*", *Korean Biochem. J.*, 19(4):377-382 (1986).
Dale, et al., "Purification and partial characterization of a highly immunogenic human leukocyte protein, the L1 antigen", *Eur. J. Biochem.*, 134:1-6 (1983).
Dogan, et al., "Process options in hepatitis B surface antigen extraction from transgenic potato", *Biotechnol. Prog.*, 16:435-441 (2000).
Hardy, et al., "Large-scale production of recombinant hepatitis B surface antigen from *Pichia pastoris*", *J. Biotechnol.*, 77:157-167 (2000).
Igarashi, et al., "A new method for purification of staphylocoagulase by a bovine prothrombin-sepharose column", *J. Biochem.*, 86:1615-1618 (1979).
Madalinski, et al., "DEAE-cellulose chromatography: A method for dissociation of soluble immune complexes of hepatitis B antigen", *J. Infect. Dis.*, 129(4):371-375 (1974).
Tleugabulova, "Size-exclusion chromatographic study of the reduction of recombinant hepatitis B surface antigen", *J. Chromatogr. B.*, 713:401-407 (1998).
Wampler, et al., "Multiple chemical forms of hepatitis B surface antigen produced in yeast", *Proc. Natl. Acad. Sci., USA*, 82:6830-6834 (1985).
Brayden et al. J. Pediatr. 2001, vol. 138: pp. 752-755.
Patriaca P. Document published by NIH, Aug. 27, 1999.
Lanford et al. 1989, vol. 63, No. 4, pp. 1549-1557.
Kennedy et al. J. Exp. Med. 1984, pp. 655-665.
Sanchez et al. Infection and Immunity 1980, vol. 980, vol. 30, No. 3, pp. 728-733.
Miyanohara et al. Proc. Natl. Acad. Sci. USA. 1983, vol. 80, pp. 1-5.
MMWR weekly, published by CDC on Sep. 10, 1999.
Thimersal in Vaccine published by US FDA.
Sigma ProductInformation of 2-mercaptoethanol p. 1-3 published on Nov. 23, 1996.
Sigmal RBI catolog for DTT on p. 823 published on 2000-2001.
Diminsky et al. Vaccine Aug. 1999, vol. 18, No. 1-2. pp. 3-17.
Yamamoto et al. (Biologicals 1997, vol. 25, pp. 373-380.
Davis et al. (J. Imumol. 1998, vol. 160, pp. 870-876.
Hitzeman et al. Nucleic Acids Research 1983, vol. 11, No. 9, pp. 2745-2763.
Michael et al Vaccine 200, vol. 19, pp. 950-957, see p. 950-951.
Gylca et al. Vaccine 2001, vol. 19, pp. 825-833, see pp. 825.

*Primary Examiner* — Bao Li
(74) *Attorney, Agent, or Firm* — Gwynedd Warren; Glaxosmithkline Global Patents

(57) ABSTRACT

The present invention relates to a method for the production of a hepatitis B antigen suitable for use in a vaccine, the method comprising purification of the antigen in the presence of cysteine, to vaccines comprising such antigens.

6 Claims, 3 Drawing Sheets

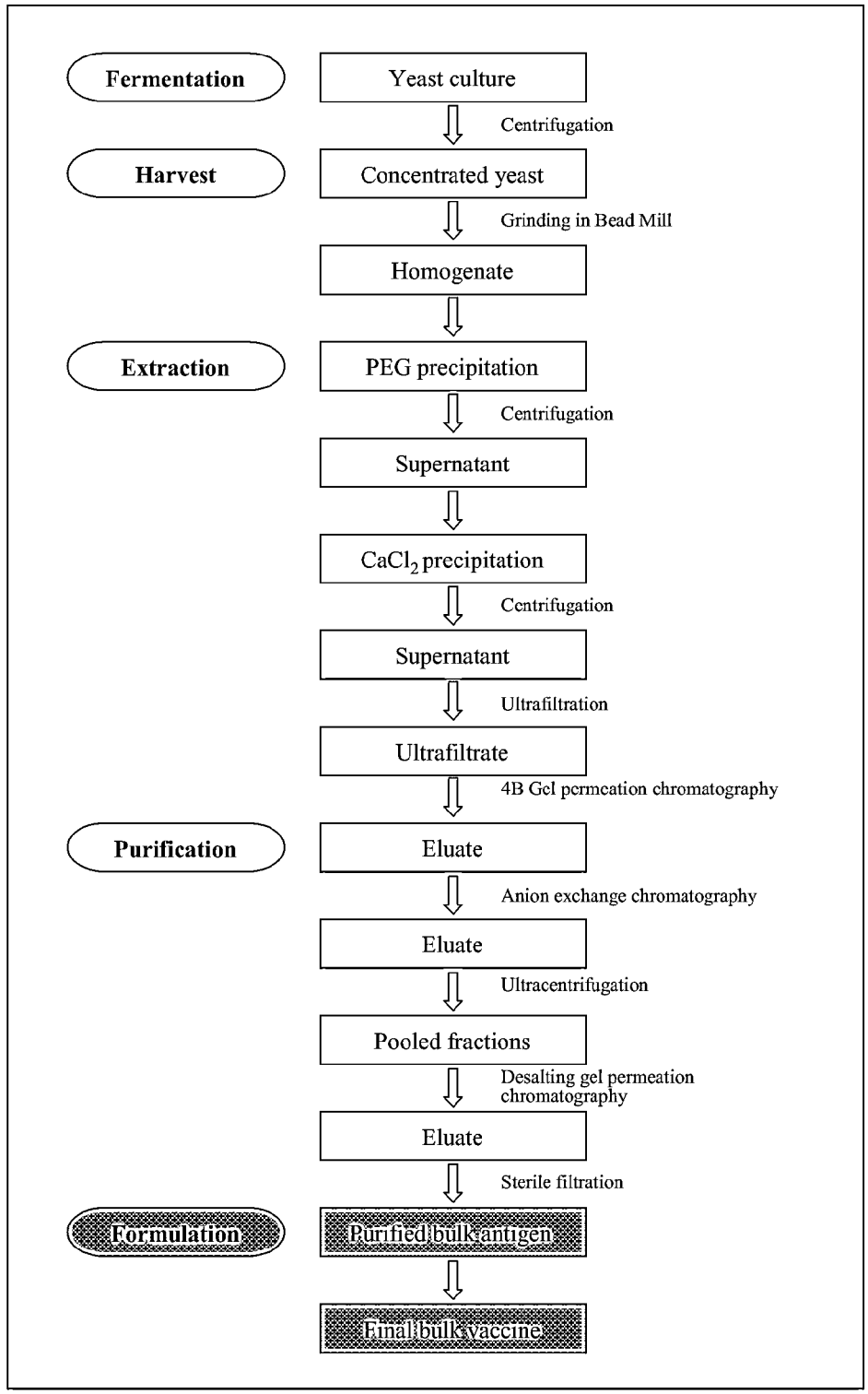
Figure 1: Flow diagram of the thiomersal free production process for Engereix B™

Figure 2: SDS-PAGE analysis of bulk antigen lots: silver staining: 1 µg protein per sample.

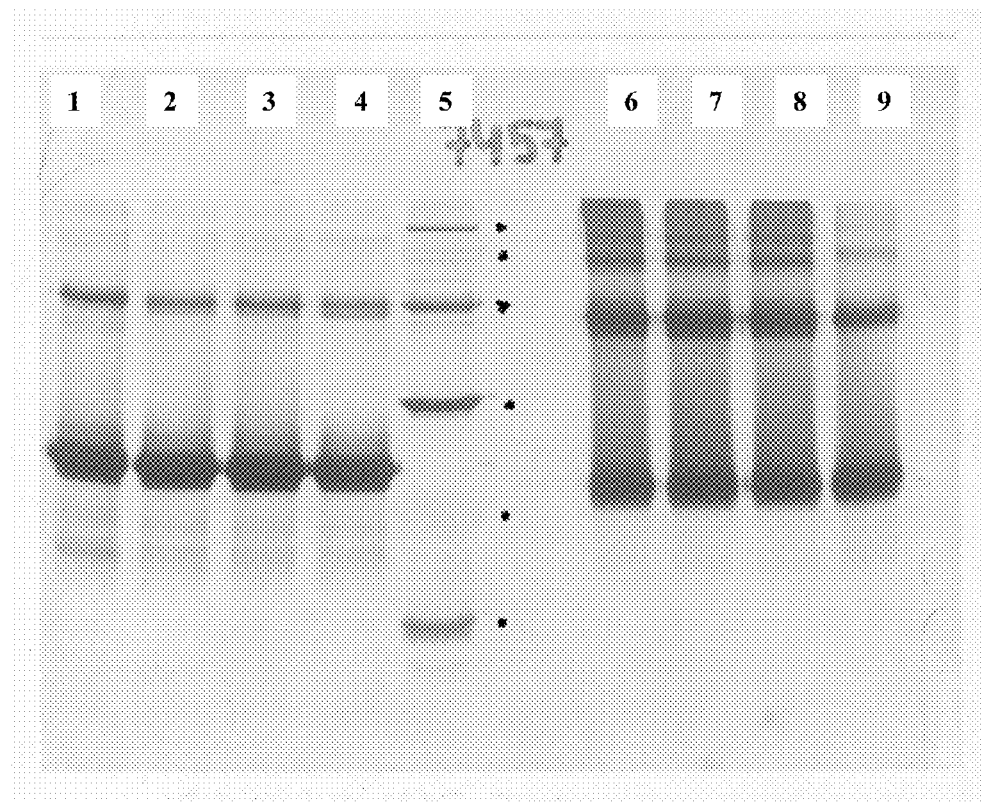

Lane 1: HEF 001, reducing conditions
Lane 2: HEF002, reducing conditions
Lane 3: HEF003, reducing conditions
Lane 4: HEP2005, reducing conditions
Lane 5: Molecular weight markers
Lane 6: HEF001, non reduced
Lane 7: HEF002, non reduced
Lane 8: HEF003, non reduced
Lane 9: HEP2055, non reduced The positions of the molecular weight markers are indicated by the black dots: 92500, 66200, 45000, 31000, 21500, 14400.

Figure 3: Residual yeast proteins in bulk antigen lots produced by the thiomersal free process: Western blotting with rabbit anti-yeast protein serum

Lane 1: Molecular weight markers (precoloured)
Lane 2: Low molecular weight markers (biotinylated)
Lane 3: HEF001, 20 mcg protein
Lane 4: HEF002, 20 mcg protein
Lane 5: HEF003, 20 mcg protein
Lane 6: HEP2055, 20 mcg protein The positions of the low molecular weight markers are indicated by black dots: 92500, 66200, 45000, 31000, 21500, 14400.

PURIFICATION OF HBV ANTIGENS FOR USE IN VACCINES

CROSS REFERENCE TO PRIOR APPLICATIONS

This application is a continuation of U.S. application Ser. No. 10/344,211, filed Jul. 18, 2003, now abandoned, which is the US National Stage 371 Application of PCT/EP01/09100, filed Aug. 7, 2001, the disclosure of which is incorporated by reference herein. This application also claims benefit of the filing dates of the Great Britain Applications No. 0101334.1 filed Jan. 18, 2001, and No. 0019728.5, filed Aug. 10, 2000.

BACKGROUND OF THE INVENTION

Chronic hepatitis B virus (HBV) infection, for which there is currently limited treatment, constitutes a global public health problem of enormous dimensions. Chronic carriers of HBV, estimated to number more than 300 million worldwide, are at risk for development of chronic active hepatitis, cirrhosis and primary hepatocellular carcinoma.

Many vaccines which are currently available require a preservative to prevent deterioration. A frequently used preservative is thiomersal which is a mercury-containing compound. Some concerns have been raised about the use of mercury in vaccines, although commentators have stressed that the potential hazards of thiomersal-containing vaccines should not be overstated (Offit; P. A. JAMA Vol. 283; No:16). Nevertheless it would be advantageous to find new and potentially safer methods of preparation of vaccines to replace the use of thiomersal in the manufacturing process. There is thus a need to develop vaccines which are thiomersal-free, in particular hepatitis B vaccines.

SUMMARY OF THE INVENTION

This invention relates to a novel process of manufacture of a hepatitis B vaccine for use in the treatment or prophylaxis of hepatitis B virus (HBV) infections. It further relates to a HBV vaccine obtainable by the novel process of the invention.

BRIEF DESCRIPTION OF THE DRAWINGS

FIG. 1 is a flow diagram illustrating the process for producing thiomersal-free Hepatitis B antigen.

FIG. 2 is an image of a PAGE analysis of bulk antigen.

FIG. 3 is an image of a western blot showing residual yeast protein following thio-free production of Hepatitis B antigen.

DETAILED DESCRIPTION OF THE INVENTION

In a first aspect the present invention provides a method for producing a hepatitis B antigen suitable for use in a vaccine, the method comprising purification of the antigen in the presence of a reducing agent comprising a free —SH group.

The present invention preferably provides a method of producing a stable hepatitis B antigen without trace of thiomersal which comprises purification of the antigen in the presence of a reducing agent having a free —SH group.

The antigen preparation is generally without trace of thiomersal when thiomersal is not detectable in the purified antigen product using absorption spectrophotometery of mercury, as described herein.

The hepatitis antigen preparation preferably comprises less than 0.025 µg mercury per 20 µg protein, suitably as measured by absorption spectrophotometery.

Preferably the purification is carried out in the absence of thiomersal, and the purified antigen is completely free of thiomersal.

Preferably the antigen is stable, suitably substantially as stable as a hepatitis antigen purified in the presence of thiomersal, as outlined in Example 1 herein for example.

Preferably the hepatitis antigen is immunogenic.

Preferably the reducing agent is added during the antigen purification process, preferably after growth of cells expressing the antigen.

Preferably the reducing agent is cysteine, dithiothreitol, β-mercaptoethanol or glutathione, with cysteine being most preferred.

Accordingly the present invention preferably provides a method of producing a stable immunogenic hepatitis B antigen without trace of thiomersal which comprises purification of the antigen in the presence of cysteine.

Preferably the purification is carried out in the presence of a cysteine solution.

Preferably, the cysteine, in solution or powder form, is added during the process to a final concentration of between 1 and 10 mM, preferably 1 to 5 mM. More preferably, the cysteine is added to a final concentration of about 2 mM.

Preferably the cysteine is L-cysteine.

The invention further provides a method of producing a stable hepatitis B antigen without trace of thiomersal wherein the crude antigen is subjected to gel permeation chromatography, subjected to ion-exchange chromatography and mixed with a reducing agent having a free —SH group.

Preferably the ion-exchange chromatography is anion-exchange chromatography.

The invention further provides a hepatitis B antigen free of thiomersal obtainable by the method of manufacture of the present invention wherein the antigen is at least as immunogenic and antigenic as the hepatitis B antigen manufactured in the presence of thiomersal.

The invention further provides an immunogenic hepatitis B antigen having a mean ELISA protein ratio greater than 1.5 and an RF1 content with at least a 3-fold lower IC50 value than that of the hepatitis B surface antigen manufactured in the presence of thiomersal.

In an further aspect the invention relates to a method for the production of a hepatitis antigen suitable for use in a vaccine, the method comprising purification of the antigen in the presence of thiomersal and subsequent treatment of antigen in the presence of a reducing agent comprising a free —SH group.

Suitably the treatment is followed by a purification step such as a dialysis step to remove thiomersal.

Preferably the reducing agent is cysteine, DTT, glutathione or 2-mercaptoethanol.

The hepatitis B antigen of the invention may be used for either the treatment or prophylaxis of hepatitis B infections, especially treatment or prophylaxis, for example, of chronic hepatitis B infections.

The present invention further provides a vaccine formulation comprising a hepatitis B antigen of the present invention in conjunction with an adjuvant. Preferably the adjuvant is an aluminium salt or a preferential stimulator of TH1 cell response.

Preferably the antigen is a hepatitis B surface antigen.

The preparation of hepatitis B surface antigen is well documented. See for example, Harford et. al. in Develop. Biol. Standard 54, page 125 (1983), Gregg et. al. in Biotechnology, 5, page 479 (1987), EP-A-0 226 846, EP-A-0 299 108 and references therein.

As used herein the expression 'hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et. al. Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703.

HBsAg may also refer to polypeptides described in EP 0 198 474 or EP 0 304 578.

Normally the HBsAg will be in particle form. In a particularly preferred embodiment the HbsAg will consist essentially of the HbsAg S-antigen mentioned hereinabove.

The vaccine may advantageously include a pharmaceutically acceptable excipient such as a suitable adjuvant. Suitable adjuvants are commercially available such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In the formulations of the invention it is preferred that the adjuvant composition induces an immune response predominantly of the TH1 type. High levels of Th1-type cytokines (e.g., IFN-γ, TNFα, IL-2 and IL-12) tend to favour the induction of cell mediated immune responses to an administered antigen. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Accordingly, suitable adjuvants for use in eliciting a predominantly Th1-type response include, for example a combination of monophosphoryl lipid A, preferably 3-de-O-acylated monophosphoryl lipid A (3D-MPL) together with an aluminium salt. Other known adjuvants which preferentially induce a TH1 type immune response include CpG containing oligonucleotides. The oligonucleotides are characterised in that the CpG dinucleotide is unmethylated. Such oligonucleotides are well known and are described in, for example WO 96/02555. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

A particularly potent adjuvant formulation involving QS21, 3D-MPL & tocopherol in an oil in water emulsion is described in WO 95/17210 and is a preferred formulation.

Accordingly in one embodiment of the present invention there is provided a vaccine comprising a hepatitis B surface antigen of the present invention, which additionally comprises a TH-1 inducing adjuvant. A preferred embodiment is a vaccine in which the TH-1 inducing adjuvant is selected from the group of adjuvants comprising: 3D-MPL, QS21, a mixture of QS21 and cholesterol, and a CpG oligonucleotide. Another preferred embodiment is a vaccine comprising a hepatitis B surface antigen adjuvanted with a monophosphoryl lipid A or derivative thereof, QS21 and tocopherol in an oil in water emulsion.

Preferably the vaccine additionally comprises a saponin, more preferably QS21. Another particular suitable adjuvant formulation including CpG and a saponin is described in WO 00/09159 and is a preferred formulation. Most preferably the saponin in that particular formulation is QS21. Preferably the formulation additionally comprises an oil in water emulsion and tocopherol.

The present invention further provides a vaccine formulation comprising a hepatitis B surface antigen of the present invention in conjunction with an adjuvant and additionally comprising one or more antigens selected from the group consisting of: diptheria toxoid (D), tetanus toxoid (T) acellular pertussis antigens (Pa), inactivated polio virus (IPV), *haemophilus influenzae* antigen (Hib), hepatitis A antigen, herpes simplex virus (HSV), chlamydia, GSB, HPV, *streptococcus pneumoniae* and *neisseria* antigens. Antigens conferring protection for other diseases may also be combined in the vaccine formulation of the present invention.

In one particular embodiment, the vaccine formulation comprises a hepatitis B surface antigen obtainable by the method of manufacture of the present invention in conjunction with an adjuvant and an inactivated polio virus.

The present invention also provides a method of treatment and/or prophylaxis of hepatitis B virus infections, which comprises administering to a human or animal subject, suffering from or susceptible to hepatitis B virus infection, a safe and effective amount of a vaccine of the present invention for the prophylaxis and/or treatment of hepatitis B infection.

The invention further provides the use of a hepatitis B surface antigen of the present invention in the manufacture of a medicament for the treatment of patients suffering from a hepatitis B virus infection, such as chronic hepatitis B virus infection.

The vaccine of the present invention will contain an immunoprotective quantity of the antigen and may be prepared by conventional techniques.

Vaccine preparation is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Use of Quil A is disclosed by Dalsgaard et al., *Acta Vet Scand,* 18:349 (1977). 3D-MPL is available from Ribi immunochem, USA, and is disclosed in British Patent Application No. 2220211 and U.S. Pat. No. 4,912,094. QS21 is disclosed in U.S. Pat. No. 5,057,540.

The present invention is illustrated by but not limited to the following examples, wherein:

FIG. 1 illustrates the thiomersal free production process for Engerix B™;

FIG. 2 illustrates SDS-PAGE analysis of bulk antigen lots; and

FIG. 3 illustrates residual yeast proteins in bilk antigen lots produced by the thiomersal free process.

EXAMPLES

Example 1

Production Process of Hepatitis B Surface Antigen in the Presence of Thiomersal

The Hepatitis B surface antigen (HBsAg) of SB Biologicals hepatitis B monovalent vaccine (Engerix B™) is expressed as a recombinant protein in *Saccharomyces cerevisiae* (see Harford et al. loc. cit.). The 24 kD protein is produced intracellularly and accumulated in the recombinant yeast cells. At the end of the fermentation the yeast cells are harvested and disrupted in the presence of a mild surfactant such as Tween 20 to liberate the desired protein. Subsequently the cell homogenate, containing the soluble surface antigen particles, is prepurified in a series of precipitations and then concentrated via ultrafiltration.

Further purification of the recombinant antigen is performed in subsequent chromatographic separations. In a first step the crude antigen concentrate is subjected to gel permeation chromatography on Sepharose 4B medium. Thiomersal is present in the elution buffer at the 4B gel permeation chromatography step. The elution buffer has the following composition: 10 mM Tris, 5% ethylene glycol, pH 7.0, 50 mg/L thiomersal. Thiomersal is included in this buffer to control bioburden. Most of this thiomersal is removed during the subsequent purification steps including ion exchange chromatography, ultracentrifugation and desalting (gel permeation) so that purified bulk antigen preparations prepared by the original process contain about 1.2 µg and less than 2 µg of thiomersal per 20 µg of protein.

An Ion-Exchange chromatography step is performed using a DEAE-matrix and this pool is then subjected to a Cesium-gradient ultracentrifugation on 4 pre-established layers of different Cesium chloride concentrations. The antigen particles are separated from contaminating cell constituents according to their density in the gradient and eluted at the end of the centrifugation process. Cesium chloride is then removed from this pool by a second gel permeation on Sepharose gel.

When HBsAg is prepared by the process containing thiomersal in the 4B gel permeation buffer, protein concentrations of over 30 mg/ml are recovered in the pooled HBsAg containing fractions from the CsCl gradient, corresponding to an equivalent concentration of HBsAg as assayed by the AUSZYME kit from Abbott Laboratories.

The CsCl ultracentrifugation step usefully eliminates residual lipids, DNA and minor protein contaminants from the HBsAg preparation. It is performed by zonal centrifugation in a Ti 15 rotor from Beckman Instruments, Fullerton, Calif. at a speed of 30,000 rpm for about 40 to 60 hours. The sample to be purified is applied to layers of CsCl solution with final concentrations of 0.75, 1.5, 2.5 and 3.25 M CsCl. At the end of centrifugation the gradient is eluted into fractions. Fractions containing HBsAg may be identified by UV absorbance at 280 nm or by testing dilutions of the fractions with the AUSZYME kit. The HBsAg band is at a density of 1.17 to 1.23 g/cm$^3$.

The solution containing the purified HBsAg is sterile filtered before being used to make a vaccine formulation.

Purification from the yeast cell lysate is complex as the antigen is produced intracellularly and a series of separation techniques designed to eliminate different types of (yeast) contaminants are necessary to obtain pure bulk antigen. The steps of purification are important, as the product to be purified is a lipoprotein particle containing multiple copies of the surface antigen polypeptide and this structure must be maintained throughout the purification process. It is a particularity of this process that it yields surface antigen particles which are fully immunogenic without the need for further chemical treatment to enhance immunogenicity (compare EPO135435).

The details of the production process are further described in European Patent 0199698.

Example 2

Production and Characterization of Yeast-Derived HBsAg by a Thiomersal Free Process 1. Production and Purification of Yeast-Derived HBsAg
1.1 Outline of the Production Process Hepatitis B surface antigen may be produced by fermentation of an appropriate strain of *Saccharomyces cerevisiae*, for example that described in Harford et. al. (loc. cit.).

At the end of large-scale fermentation of the recombinant yeast strain, the cells are harvested and broken open in the presence of a mild surfactant such as Tween 20. The surface antigen is then isolated by a multistep extraction and purification procedure exactly as described above in Example 1 up to the step of the first gel permeation on Sepharose 4B.
1.2 Thiomersal-Free Purification Process In the thiomersal free process the following two changes have been introduced compared to the process described in Example 1.

1. The elution buffer at the 4B gel permeation chromatography step no longer contains thiomersal.

2. Cysteine (2 mM final concentration) is added to the eluate pool from the anion exchange chromatography step.

It was found that omission of thiomersal from the 4B gel permeation buffer may result in precipitation of the HBsAg particles during the CsCl density gradient centrifugation step with loss of product and aggregation or clumping of the recovered antigen.

Addition of cysteine at 2 mM final concentration to the eluate pool from the preceding anion exchange chromatography step prevents precipitation and loss of antigen during CsCl density centrifugation.

2. Cysteine is a preferred substance for this treatment as it is a naturally occurring amino acid and can be removed at the subsequent desalting step on a gel permeation column using Sepharose 4BCLFF as the column matrix.

There are no other changes in the manufacturing process compared to the process described in Example 1.

The thiomersal free process yields bulk antigen of a purity and with properties comparable to antigen from the process of Example 1.
1.2a The thiomersal added to the 4B buffer at 50 µg/ml is thought to decompose and the resulting ethyl mercury may attach covalently to free sulphydryl groups on cysteine residues of the protein. The protein contains 14 cysteine residues of which 7 are located between positions 101 and 150.

This region of the protein is believed to be located at the surface of the particle and contain the major antigenic region of HBsAg including the immunodominant a region and the recognition site for the RF1 monoclonal antibody (Waters J et al, Postgrad. Med. J., 1987:63 (Suppl. 2): 51-56. and Ashton-Rickardt and Murray J. Med. Virology, 1989:29:196). Antigen purified with thiomersal present in the 4B gel permeation buffer contains about 0.5-0.6 µg mercury at the end of the purification process. This mercury is not fully removed by simple dialysis.

In one experiment, 0.56 µg Mercury per 20 µg protein was measured on bulk antigen preparation. This preparation was dialysed for 16 hours at room temperature against 150 mM NaCl, 10 mM NaPO$_4$ buffer pH 6.9. At the end of dialysis, a concentration of 0.33 µg Hg per 20 µg protein was measured.

In contrast, dialysis in the presence of a reducing agent such as L-cysteine at 0.1 to 5.0 mg/ml, DTT at 50 mM or 2-mercaptoethanol at 0.5 M, followed by a second dialysis to remove the reducing agent, results in reduction of the mercury content of the antigen preparation to less than 0.025 µg Mercury per 20 µg protein. This is the lowest limit of detection of the method.

The mercury content was determined by absorption spectrophotometry. The antigen is diluted in a solution containing 0.01% w/v of potassium bichromate ($K_2Cr_2O_7$) and 5% v/v of nitric acid. Standard solutions are prepared with thiomersal as the mercury source. The atomic absorption of sample and standard solutions is measured after vaporisation in a vapour generator, with a mercury-specific cathode at 253.7 nm. Atomic absorption of the dilution liquid is measured as blank. The mercury content of the sample is calculated via the calibration curves obtained from the standard solutions. Results are expressed as µg of mercury per 20 µg of protein.

1.3 Production of Thiomersal Free Bulk Antigen

The process steps for purification of bulk antigen are shown in FIG. 1.

1.4 Composition of Vaccine Formulated without Thiomersal.

A typical quantitative composition for a hepatitis B vaccine without preservative and formulated from antigen prepared by the thiomersal free process is provided in Table 1.

TABLE 1

| Constituent | Amount per ml |
|---|---|
| Active constituent - Protein of which at least 95% is HBsAg | 20 µg |
| Aluminium hydroxide (adsorbent) (expressed as Al$_2$O$_3$) | 0.95 mg |
| Sodium chloride | 9.0 mg (maximum) |
| Disodium phosphate dihydrate | 0.98 mg |
| Sodium dihydrogen phosphate dihydrate | 0.71 mg |
| Water for injection q.s. ad | 1.0 ml |

The composition may be varied by the addition of 3D-MPL and/or other adjuvants.

2. Characterization of Bulk Antigen and Vaccine Produced by the Thiomersal Free Process 2.1. Tests and Assays on Purified Bulk Antigen 2.1.1 Basis of Comparison Three lots of bulk antigen were prepared by the thiomersal free process according to this example (Example 1.2) and are identified as HEF001, HEF002 and HEF003. These were compared to a lot of bulk antigen (HEP2055) prepared by the previous process (as described in Example 1) in the presence of thiomersal.

2.1.2 Tests and Assays on Bulk Antigen

The three bulk antigen lots produced by the thiomersal free process were tested and the results are summarised in Table 2.

Protein content was measured by the method of Lowry et al (J. Biol. Chem. 1951:193:265).

Endotoxin content was measured by a *Limulus* gel clotting technique using a commercially available kit from Cape Cod Associates, 704 Main St., Falmouth, Mass. 02540, USA. The reagent is standardized against the US Pharm. Endotoxin Reference Standard.

Tween 20 was measured by the method of Huddleston and Allred (J. Amer. Oil Chemist Soc., 1965:42:983).

HBsAg content was measured by the commercially available AusZYME kit from Abbott Laboratories, One Abbott Park Road, Abbott Park, Ill. 60064, USA. Assay procedure B of the manufacturer was employed. A batch of bulk antigen purified by the process containing thiomersal was used as a standard to establish the dose response curve.

Polysaccharides were measured by the method of Dubois et al (Anal. Chem. 1956:28:350).

Lipids were measured using a commercially available kit (Merkotest Total Lipids 3321) from E. Merck, B. P. 4119, Darmstad D-6100, Germany.

DNA content was measured by the Threshold method using apparatus and reagents available from Molecular Devices Corp., Gutenbergstraβe 10, Ismaning, Munich, Germany.

The values found in the tests and assays are in the range seen for bulk antigen lots manufactured using thiomersal in the elution buffer of the Sepharose 4B gel permeation step, with the exception of the antigenic activity by ELISA. The values for this measurement for the three HEF preparations are higher (1.63-2.25) than that found for the bulk antigen lot HEP2055 which has a ELISA/protein ratio of 1.13. The ELISA/protein ratios measured by the AUSZYME kit for thiomersal containing batches of bulk antigen are generally about 1.0 and within the range 0.8-1.2 and very rarely exceed 1.4.

2.1.3 SDS-PAGE Gel Analysis

The bulk antigen preparations were assayed by SDS-PAGE analysis in reducing conditions and Coomassie blue staining. All samples showed a major band at 24K with traces of a dimer protein. The samples were judged to be of high purity (>99% pure) as assessed by the absence of visible bands of contaminating proteins.

Samples (1 µg) of the bulk antigen preparations were assayed by SDS-PAGE in reducing and non-reducing conditions and silver staining (FIG. 2). In reducing conditions the samples showed an intense band migrating at 24K with traces of dimer and multimeric forms. The gel patterns are indistinguishable from that of HEP2055 as comparator. The samples were also run in non-reducing conditions. In these conditions less of the material migrates at 24K and the amount of polypeptide migrating at dimeric and multimeric positions is increased. The thiomersal free bulk antigen lots appear to have a somewhat higher degree of polymerisation than the comparator HEP2055 lot.

The identity of the 24K polypeptide revealed by Coomassie blue or silver staining was confirmed by Western blotting with rabbit polyclonal antibodies raised against plasma HBsAg. The bulk antigen preparations show a major band at 24K together with dimeric and trimeric forms. The technique reveals minor traces of breakdown products of the surface antigen protein. There are no differences between the bulk antigen prepared by the thiomersal free process and the HEP2055 lot.

The presence of residual yeast proteins was assayed by SDS-PAGE analysis in reducing conditions and Western blotting with rabbit polyclonal antiserum raised against yeast proteins (FIG. 3). The technique is qualitative and does not permit quantitation of the impurities.

A constant band pattern is shown over the three bulk antigen lots prepared by the thiomersal free process and the HEP2055 lot with one exception.

A heavily staining band present at ±23K in the HEP2055 bulk antigen is virtually absent in the 3 HEF preparations. The Western blotting shows that the thiomersal free purification process results in a purer antigen product.

TABLE 2

Results of tests and assays on purified, thiomersal free bulk antigen

| TEST | RESULT | | | |
|---|---|---|---|---|
| | HEF001 | HEF002 | HEF003 | HEP2055 |
| PH | 6.8 | 6.8 | 6.8 | 6.8 |
| Protein content by Lowry | 1312 µg/ml | 888 µg/ml | 913 µg/ml | 995 µg/ml |
| Endotoxin content | <0.25 EU | <0.25 EU | <0.25 EU | <0.25 EU |
| Tween 20 content | 7.1 µg | 6.6 µg | 7.4 µg | 5.8 µg |
| Antigenic activity by ELISA | 2957 µg/ml | 1505 µg/ml | 1486 µg/ml | 1128 µg/ml |
| ELISA/protein ratio | 2.25 | 1.69 | 1.63 | 1.13 |
| Polysaccharide content | 0.33 µg | 0.35 µg | 0.33 µg | 0.34 µg |
| Lipid content | 13.7 µg | 12.8 µg | 12.9 µg | 11.8 µg |
| DNA content by Threshold | <1 pg | <1 pg | <1 pg | <1 pg |

2.1.4 Other Biochemical Tests and Assays 2.1.4.1 DNA Content

The DNA content of the 3 bulk antigen lots was measured by the Threshold method (Molecular Devices Corp). The amounts measured were less than 10 µg DNA per 20 µg protein (Table 2); the same level of DNA content seen with bulk antigen produced by the current approved process.

2.1.4.2 Amino Acid Composition

The amino acid composition of the three HEF bulk antigen lots was determined after acid hydrolysis with 6N HCl by chromatography of the amino acids on an ion exchange column with post column ninhydrin detection. Proline and tryptophan were not determined. The results are given in Table 3.

The compositions found are in good agreement with that determined on HEP2055 and with the expected composition derived from the DNA sequence. Although the number of glycine residues measured for HEP2055 is close to the expected composition, a value of 16 to 17 residues is more usually measured for bulk antigen preparations. The mean number of cysteine residues found is the expected 14, showing that no extra cysteines are bound to the particle as a result of the treatment at the CsCl gradient step.

2.1.4.3 Quantification of Free Cysteine

The quantity of free cysteine present in bulk antigen preparations obtained according to the method described was measured after oxidation of the particles with performic acid without prior acid hydrolysis. Oxidised free cysteine residues were separated on an ion exchange column with post column detection by ninhydrin. The limit of detection of cysteine by this method is 1 µg per ml.

No free cysteine could be measured in the 3 HEF antigen preparations when tested at the initial protein concentrations given in Table 2.

The technique measures both free cysteine residues present in the buffer and cysteine residues which are attached to the HBsAg protein by disulphide bonding but which do not form part of the polypeptide sequence.

2.1.4.4 N-Terminal Sequence Analysis

The presence of possible protein contaminants and degradation products in the three bulk antigen lots produced by the modified process was assessed by N-terminal sequence analysis based on Edman degradation. The N-terminal sequence MENITS . . . of the HBsAg protein was detected with no interference from other sequences. The N-terminal methionine was also confirmed to be 60-75% blocked by acetylation, as observed previously for HBsAg polypeptide produced by the routine process.

TABLE 3

Amino acid composition of HBsAg

| Amino acid | HEF001 | HEF002 | HEF003 | Mean comp. | HEP2055 | Expected comp. |
|---|---|---|---|---|---|---|
| Asp | 11.3 | 11.3 | 11.3 | 11.3 | 11.5 | 10 |
| Thr | 17.5 | 17.4 | 17.2 | 17.4 | 17.8 | 17 |
| Ser | 21.4 | 21.6 | 21.4 | 21.5 | 20.9 | 23 |
| Glu | 11 | 11 | 11 | 11.0 | 10.5 | 9 |
| Pro | nd | nd | nd | | nd | 24 |
| Gly | 17.1 | 16.8 | 16.7 | 16.9 | 14.6 | 14 |
| Ala | 7.5 | 7.4 | 7.4 | 7.4 | 7.2 | 6 |
| Cys | 12.3 | 14.95 | 14.9 | 14.1 | 13.2 | 14 |
| Val | 10.9 | 11 | 10.9 | 10.9 | 10.7 | 11 |
| Met | 6.8 | 6.7 | 7.1 | 6.9 | 7.1 | 6 |
| Ile | 12.3 | 12.4 | 12.5 | 12.4 | 12.2 | 16 |
| Leu | 26.3 | 26.6 | 26.2 | 26.4 | 26.7 | 33 |
| Tyr | 6.8 | 6.8 | 6.8 | 6.8 | 7 | 6 |
| Phe | 13.8 | 13.9 | 13.8 | 13.8 | 13.9 | 15 |
| His | 3 | 2.8 | 3.3 | 3.0 | 3.3 | 1 |
| Lys | 4 | 4 | 3.9 | 4.0 | 4.2 | 3 |
| Arg | 5.7 | 5.8 | 5.7 | 5.7 | 6.1 | 5 |
| Trp | nd | nd | nd | | nd | 13 |

2.1.4.5 Laser Light Scattering Analysis

Particle size comparisons were made by laser light scattering between the HBsAg particles produced using the modified process and the HEP2055 reference lot (Table 4).

The mean molecular weights determined show good consistency between the preparations.

TABLE 4

HBsAg particle molecular weights by laser light scattering

| Antigen lot | MW (Daltons) |
|---|---|
| HEF001 | $3.07 \times 10^6$ |
| HEF002 | $2.76 \times 10^6$ |
| HEF003 | $2.76 \times 10^6$ |
| HEP2055 | $3.34 \times 10^6$ |

2.1.4.6 Electron Microscopy

The bulk antigen preparations were examined by electron microscopy after fixation and staining with uranyl acetate.

The particles observed were similar in all the samples and conformed to the ±20 nm subspherical or cobblestone-like particles typical of HBsAg. The particles observed in the 3 HEF lots were indistinguishable from HEP2055.

2.1.5 Immunological Analyses 2.1.5.1 Reactivity with RF1 Monoclonal Antibody

The three bulk antigen preparations were tested for their reactivity with the RF1 monoclonal antibody by ELISA inhibition assay. The RF1 monoclonal antibody has been shown to protect chimpanzees against challenge with HBV and is considered to recognize a protective conformational epitope on the HBsAg particle (Iwarson S et al, 1985, J. Med, Virol., 16: 89-96).

The RF1 hybridoma may be propagated in the peritoneal cavity of BalbC mice or in tissue culture.

Ascitic fluid diluted at 1/50000 in saturation buffer (PBS containing 1% BSA, 0.1% Tween 20) was mixed 1:1 with various dilutions in PBS of the HBsAg samples to be tested (final concentrations ranging between 100 µg and 0.05 µg/ml).

Mixtures were incubated in Nunc Immunoplates (96 U) for 1 hr at 37° C. before being transferred for 1 hr at 37° C. onto plates coated with a standard preparation of HBsAg. The standard HBsAg preparation was a lot of bulk antigen (Hep 286) purified by the thiomersal containing process. After a washing step with PBS containing 0.1% Tween 20, biotin-conjugated sheep anti-mouse IgG diluted 1/1000 in saturation buffer was added to and incubated for 1 hr at 37° C. After a washing step, streptavidin-biotinylated peroxydase complex diluted 1/1000 in saturation buffer was added to the same wells and incubated for 30 min at 37° C. Plates were washed and incubated with a solution of OPDA 0.04%, $H_2O_2$ 0.03% in 0.1 M citrate buffer pH 4.5 for 20 min at room temperature. The reaction was stopped with $2NH_2SO4$ and the optical densities (O.D.) were measured at 490/630 nm and plotted graphically.

The IC50, defined as the concentration of antigen (inhibitor concentration) that inhibits 50% of the antibody binding to coated HBsAg was calculated using a 4 parameters equation and expressed in ng/ml.

A series of HEP antigen lots including HEP2055 were also tested, together with the Herpes simplex gD antigen as negative control. The assay measures the ability of each test antigen to inhibit binding of RF1 to a standard antigen preparation (HEP286) bound to microtitre plates.

Table 5 gives the concentrations of each antigen found to inhibit 50% of RF1 binding to the fixed antigen.

TABLE 5

Inhibition of binding of RF1 monoclonal antibody to HBsAg

| Bulk antigen | IC50 (ng/ml)* |
|---|---|
| HEP286 | 3834 |
| HEP673 | 3437 |
| HEP720 | 3150 |
| HEP2055 | 2384 |
| HEF001 | 468 |
| HEF002 | 574 |
| HEF003 | 540 |

*IC50 = antigen concentration (ng/ml) inhibiting 50% of RF1 binding to fixed antigen The results show that 4 to 7 fold less HEF antigen is required to inhibit RF1 binding (Table 5). This shows that antigen prepared by the modified process has an increased presentation of the RF1 epitope compared to HEP bulk antigen.

The same type of inhibition assay was performed using human sera from Engerix B™ vaccines instead of the RF1 mAb and did not reveal differences between the HEP antigen lots and the HEF antigens.

2.1.5.2. Affinity of Binding to Monoclonal RF1

The kinetic parameters of RF1 monoclonal antibody binding to the 3 HEF antigen lots and to HEP2055 were measured by surface plasmon resonance using a Biacore 2000 apparatus from Amersham Pharmacia Biotech, Amersham Place, Little Chalfont, Bucks, UK.

The kinetic parameters measured were:
ka: the association rate constant ($M^{-1} S^{-1}$)
kd: the dissociation rate constant ($S^{-1}$)
Ka: the equilibrium or affinity constant ($M^{-1}$)
where $$Ka = \frac{ka}{kd}$$

The values found are given in Table 6.

TABLE 6

Affinity constants of RF1 binding to HBsAg

| Bulk antigen | ka ($\times 10^{-3}$) | kd ($\times 10^5$) | Ka ($\times 10^{-7}$) |
|---|---|---|---|
| HEF001 | 6.81 | 3.21 | 21.97 |
| HEF002 | 6.89 | 3.73 | 18.83 |
| HEF003 | 7.39 | 4.67 | 15.80 |
| HEP2055 | 3.31 | 6.30 | 5.31 |

The three HEF antigen lots gave similar association/dissociation constants and binding affinity values. In contrast HEP2055 has a weaker affinity for binding to RF1.

This is consistent with the results from the ELISA inhibition assay which showed that antigen prepared by the thiomersal free process had an increased presentation of the RF1 epitope.

2.2. Test and Assays on Vaccine Formulated with Antigen Produced by the Modified Process The three HEF antigen lots were adsorbed onto aluminium hydroxide and formulated as vaccine according to the composition as shown in Table 1. The presentation is the adult dose in vials (20 □g antigen protein in 1 ml). The lots are identified as DENS001A4, DENS002A4 and DENS003A4.

Vaccine potency was measured by an in-vitro antigen content assay using the Abbott Laboratories AUSZYME ELISA kit and a classical lot of vaccine formulated with 50 □g/ml thiomersal as standard. Vaccine potency was measured using method B as described in PharmaEuropa Special Issue Bio97-2 (December 1997). The three HEF lots give high values for antigen content, nearly twice the stated content of 20 μg antigen protein.

2.2.1 Reactivity of DENS Vaccine with RF1 Monoclonal Antibody

The antigenicity of the adsorbed vaccine was further tested in an inhibition assay with RF1 monoclonal antibody. The assay measures the ability of the vaccine sample to inhibit RF1 binding to fixed bulk antigen (HEP286).

Ascitic fluid diluted at 1/50000 in saturation buffer (PBS containing 1% BSA, 0.1% Tween 20) was mixed 1:1 with various dilutions in PBS of the vaccine samples to be tested (concentration ranging between 20 μg and 0.05 μg/ml).

Mixtures were incubated in Nunc Immunoplates (96 U) for 2 hr at 37° C. with agitation before being transferred onto HBsAg coated plates. The HBsAg preparation used for coating was a lot of bulk antigen (Hep 286) purified by the thiomesal containing process. These plates are then incubated for 2 hr at 37° C. with agitation. After a washing step with PBS containing 0.1% Tween 20, biotin-conjugated sheep anti-mouse IgG diluted 1/1000 in saturation buffer was added and incubated for 1 hr at 37° C. After a washing step, streptavidin-biotinylated peroxydase complex diluted 1/1000 in saturation buffer was added to the wells and incubated for 30 min at 37° C. Plates were washed and incubated for 20 min at room temperature with a solution containing OPDA 0.04%, $H_2O_2$ 0.03% in 0.1 M citrate buffer pH 4.5. The reaction was stopped with $2NH_2SO_4$ and optical densities (O.D.) were measured at 490/630 nm and plotted graphically.

The IC50, defined as the concentration of antigen (inhibitor concentration) that inhibits 50% of the antibody binding to coated HBsAg was calculated using a 4 parameters equation and expressed in ng/ml.

Vaccine prepared from bulk antigen produced by the modified process was compared to Engerix B™ vaccine formulated from classical HEP bulk antigen and without thiomersal as preservative.

The assays were run in triplicate.

The results are given in Table 7 and show that about half the quantity of DENS vaccine is required to achieve 50% inhibition of RF1 binding as compared to preservative free Engerix B™ vaccine. This reflects an increased presentation of the RF1 epitope on the HEF/DENS antigen and is consistent with the tests done with RF1 antibody on the purified bulk antigen.

TABLE 7

Inhibition of RF1 binding by formulated vaccine

| | IC-50 (ng/ml) [1] | | | |
|---|---|---|---|---|
| | Experiment | | | |
| Vaccine lot | 1 | 2 | 3 | Mean |
| DENS001A4 | 913 | 662 | 603 | 726 |
| DENS002A4 | 888 | 715 | 521 | 708 |
| DENS003A4 | 817 | 685 | 582 | 695 |
| ENG5100A2 | 1606 | 1514 | 1481 | 1534 |
| ENG3199B9 | 1329 | 1170 | 1286 | 1262 |
| ENG3328A9 | 1417 | 1194 | 1334 | 1315 |

[1] concentration of vaccine inhibiting 50% of RF1 antibody binding to fixed antigen 2.2.2 Immunogenicity of DENS Vaccine in Mice A study was performed in Balb/C mice in order to compare the immunogenicity of the three DENS consistency lots to Engerix B™ produced according to the current antigen manufacturing process and formulated with thiomersal.

The following lots were tested:
DENS001A4
DENS002A4
DENS003A4
ENG2953A4/Q as reference Briefly, groups of 12 mice were immunised intramuscularly twice at 2 weeks interval with vaccine doses corresponding to 1/10 (2 μg) or 1/50 (0.4 μg) of the adult human dose. Antibody response to HBsAg and the isotypic profile induced by vaccination were monitored from sera taken at day 28.

Experimental Design

Groups of 12 Balb/C mice were immunised intramuscularly in both legs (2×50 μl) on days 0 and 15 with the following vaccine doses:

TABLE 8

Groups and vaccine dose

| Group | Vaccine | Volume | Antigen dose |
|---|---|---|---|
| 1 | DENS001A4 | 100 μl | 2 μg |
| 2 | →Diluted 5X in PO4/NaCl | 100 μl | 0.4 μg |
| 3 | DENS002A4 | 100 μl | 2 μg |
| 4 | →Diluted 5X in PO4/NaCl | 100 μl | 0.4 μg |
| 5 | DENS003A4 | 100 μl | 2 μg |
| 6 | →Diluted 5X in PO4/NaCl | 100 μl | 0.4 μg |
| 7 | ENG2953A4/Q | 100 μl | 2 μg |
| 8 | →Diluted 5X in PO4/NaCl | 100 μl | 0.4 μg |

On days 15 (2 weeks post 1) and 28 (2 weeks post 11) blood was taken from the retroorbital sinus.

For the design of this experiment (4 formulations×2 doses with 12 mice per group), the power was estimated a priori with the PASS statistical program. The PASS (Power and Sample Size) statistical programme was obtained from NCSS, 329 North 1000 East, Kaysville, Utah 84037. For the 2 way analysis of variance, a 2.5 fold difference of GMT between formulations with an alpha error of 5% should be detected with a power>90%.

Results

Serology:

Humoral responses (Total Ig and isotypes) were measured by ELISA assay using HBsAg (Hep286) as coating antigen and biotin conjugated anti-mouse antibodies to reveal anti-HBs antibody binding. Only post II sera were analysed.

Table 9 shows the mean and GMT anti-HBs Ig antibody responses measured on individual sera at 2 weeks post II Comparable antibody responses are induced by the DENS and classical hepatitis B formulations: GMT ranging between 2304 and 3976 EU/ml for the DENS lots compared to 2882 EU/ml for SB Biologicals hepatitis B monovalent vaccine (Engerix B™) at the 2 μg dose, and GMT ranging between 696 and 1182 EU/ml for the DENS lots compared to 627 EU/ml for SB Biologicals hepatitis B monovalent vaccine (Engerix B™) at the 0.4 μg dose.

As expected a clear antigen dose range effect is observed for all formulations at the 2 μg and 0.4 μg doses with a 3 to 6 fold difference in GMTs.

Four non responder mice (titers<50 EU/ml) were observed without clear links to the antigen doses or lots used for the injection (Groups 1, 2, 3 and 8; one mouse per group). Based on statistical analysis (Grubbs Test) these mice were discarded from further analysis.

TABLE 9

Antibody response in mice at day 28 (2 weeks post II)

| | | | | ELISA TITERS (Ig) | |
|---|---|---|---|---|---|
| Group | Vaccine | Dose | Number | Mean | GMT |
| 1 | DENS001A4 | 2 μg | 11 | 3466 | 2971 |
| 2 | | 0.4 μg | 11 | 1283 | 1182 |
| 3 | DENS002A4 | 2 μg | 11 | 2436 | 2304 |
| 4 | | 0.4 μg | 12 | 984 | 786 |
| 5 | DENS003A4 | 2 μg | 12 | 4583 | 3976 |
| 6 | | 0.4 μg | 12 | 997 | 696 |
| 7 | ENG2953A4/Q | 2 μg | 12 | 3999 | 2882 |
| | | 0.4 μg | 11 | 737 | 627 |

Statistical Analysis:

A 2 way-analysis of variance was performed on the anti-HBs titers after log transformation of post 11 data, using the vaccines (4 lots) and antigen doses (2 μg and 0.4 μg) as factors. This analysis confirmed that a statistically significant difference was observed between the two antigen doses (p value<0.001) and did not show any significant difference between the vaccine lots (p value=0.2674). As previously mentioned the power was estimated a priori and the design of the experiment was such that a 2.5 fold difference of GMT with a alpha error of 5% could be detected between formulations with a power>90%.

Isotypic Profile:

Table 10 shows the isotypic repartition (IgG1, IgG2a and IgG2b) calculated from an analysis on pooled sera at post II.

As expected, a clear TH2 response is induced by these alum based vaccines as mainly IgG1 antibodies are observed.

No difference is observed between the DENS lots or SB Biologicals hepatitis B monovalent vaccine in term of isotypic profile.

TABLE 10

Repartition of IgG isotypes in pooled day 28 sera

| Group | Vaccine | Dose | Isotype (%) | | |
|---|---|---|---|---|---|
| | | | IgG1 | IgG2a | IgG2b |
| 1 | DENS001A4 | 2 μg | 91 | 4 | 5 |
| 2 | | 0.4 μg | 87 | 8 | 5 |
| 3 | DENS002A4 | 2 μg | 97 | 2 | 1 |
| 4 | | 0.4 μg | 87 | 6 | 7 |
| 5 | DENS003A4 | 2 μg | 98 | 1 | 1 |
| 6 | | 0.4 μg | 93 | 4 | 3 |
| 7 | ENG2953A4/Q | 2 μg | 88 | 8 | 4 |
| | | 0.4 μg | 88 | 9 | 3 |

Example 3

Formulation of Combined Vaccines

The bulk antigen of the invention is particularly suitable for formulation in a combined vaccine comprising IPV.

Stability studies performed on initial lots of a combined DTPa-HBV-IPV vaccine indicated a decline in potency of the IPV component, particularly of type 1 poliomyelitis antigen, when using an in vitro immunoassay (determination of D-antigen content by ELISA) and an in vivo rat potency test. No potency loss was observed for type 3. For type 2, the potency loss was within the expected range (not more than 10% loss per year of storage).

Studies were initiated to determine the cause of this loss of potency in the combined DTPa-HBV-IPV vaccine. From the observation that the stability of IPV in SB Biologicals' DTPa-IPV vaccine is satisfactory (not more than 10% antigen content loss per year of storage), it was concluded that the HBV component was likely to be responsible for the instability of IPV in the DTPa-HBV-IPV vaccine.

The HBV component used in the initial DTPa-HBV-IPV formulation is the purified r-DNA, yeast-derived HBsAg also used for the manufacture of SB Biologicals hepatitis B monovalent vaccine and prepared as described in Example 1.

As a first attempt to determine which element in the HBV component was deleterious to IPV, the HBsAg bulk was analysed for the presence of thiomersal. It has been previously found (Davisson et al., 1956, J. Lab. Clin. Med. 47: 8-19) that thiomersal used as preservative in DTP vaccines "was detrimental to the poliomyelitis virus" in a DTP-IPV combination. This observation was considered by vaccine manufacturers who have replaced thiomersal with other preservatives to formulate their IPV-containing vaccines. More recently, the effect of thiomersal on IPV potency under conditions of long-term storage at +4° C. was reinvestigated. The loss of potency of type 1 polio virus antigen to undetectable levels after 4-6 months was reported (Sawyer, L. A. et al. 1994, Vaccine 12: 851-856).

Using atomic adsorption spectroscopy, approximately 0.5 μg of mercury (Hg) per 20 μg of HBsAg was detected in antigen purified according to Example 1.

This amount of mercury (as thiomersal and ethylmercury chloride, the thiomersal degradation product) can reduce to undetectable levels the ELISA response for D-antigen type 1 content in an IPV bulk concentrate incubated at 37° C. for 7 days.

A method was established to release mercury present in the HBsAg bulk. It was postulated that mercury could be bound to thiol groups on the HBsAg particle and could therefore be released in the presence of reducing agents. After experimentation with other reducing agents, L-Cysteine was selected as the agent for release of mercury from the HBsAg particle. After dialysis of HBsAg bulk against saline solution containing 5.7 mM L-Cysteine, no mercury was detected in the retentate (detection limit of the testing method: 25 ng Hg/20 μg HBsAg). The dialysed antigen was mixed with IPV bulk concentrate and the stability of the type 1 virus was assessed by measuring the D-antigen content after incubation at 37° C. for 7 days. The IPV bulk concentrate non-mixed and mixed with HBsAg not treated with cysteine were used as controls. The reference ELISA titer was obtained on the samples stored at +2° C. to +8° C. for 7 days. The results are summarised in Table 11:

TABLE 11

| Sample | D-antigen content (type 1)[1] | | |
|---|---|---|---|
| | 7 days/4° C. | 7 days/37° C. | Loss |
| IPV (non-mixed) | 31.6 | 24.2 | 23% |
| IPV + HBsAg not treated | 31.1 | 18.1 | 42% |
| IPV + HBsAg-cysteine-treated | 31.4 | 27.6 | 12% |
| IPV + thiomersal (1 μg/ml) | 30.5 | 11.0 | 74% |

[1]expressed in D-antigen units (DU)

The data obtained on these laboratory preparations clearly demonstrate that the stability of the type 1 polio virus is significantly improved if HBsAg is treated with cysteine to remove residual mercury prior to mixing with IPV.

The data presented above also show a loss of D-antigen content of 23% for the reference IPV preparation after incubation for 7 days at 37° C. This confirms the inherent instability of the type 1 Mahoney polio virus, as previously reported (Sawyer, L. A. et al. (1994), Vaccine 12: 851-856).

Although commercial lots of DTPa-HBV-IPV and DTPa-HBV-IPV/Hib vaccines have been prepared using a dialysis process with 5.7 mM L-Cysteine to remove residual mercury and preserve the stability of IPV, the dialysis process is not suited to large scale production and involves a series of supplementary steps to prepare thiomersal or mercury free HBsAg. In contrast, the HBsAg of the present invention, prepared without thiomersal, may be directly used in formulations of combined vaccines especially those containing IPV.

4. Summary

The previously used process for purification of yeast-derived surface antigen contains a gel permeation step where the mercury containing anti-microbial compound thiomersal is included in the elution buffer to control bioburden.

The thiomersal is not completely cleared during the subsequent steps of the process so that about 1.2 μg thiomersal per 20 μg protein is present in the purified bulk antigen.

In order to produce a completely thiomersal (mercury) free bulk antigen the purification process has been altered at two steps.

Thiomersal is omitted from the elution buffer at the 4B gel permeation step.

Cysteine (2 mM final concentration) is added to the eluate pool from the anion exchange chromatography step. This prevents precipitation of antigen during CsCl density gradient centrifugation.

There are no other changes to the production process.

The bulk antigen produced by the modified process has been characterized. Physico-chemical tests and assays show that the thiomersal free antigen is indistinguishable in its properties from antigen produced by the previously used process. The antigen particles have the same constituents.

The identity and integrity of the HBsAg polypeptide is unaffected by the modified process as judged by SDS-PAGE analysis, Western blotting using polyclonal anti-HBsAg antibodies, N-terminal sequence analysis and amino acid composition. Electron microscopy and laser light scattering analysis show that the particles are of the typical form and size expected for yeast-derived HBsAg. Analysis by Western blotting with anti-yeast protein serum shows that the antigen produced by the thiomersal free process has a similar pattern of contaminating yeast proteins. However, the amount of a contaminating band migrating at 23K is greatly reduced in the 3 HBsAg lots produced using the modified process.

Immunological analyses show that the thiomersal free particles have an increased antigenicity. The particles are more reactive with the Abbott AUSZYME kit (containing a mixture of monoclonal antibodies) giving ELISA/protein ratios of 1.6 to 2.25. This increased antigenicity is also shown with the protective RF1 monoclonal antibody. About 4 to 7 fold less thiomersal free antigen is required to inhibit RF1 binding to a standard fixed antigen. The thiomersal free and classical antigen inhibition of binding curves fall into two distinct families. This difference is also shown by measurements of the binding affinity constant for RF1 using surface plasmon resonance. The binding affinities of the thiomersal free preparations are 3 to 4 fold higher compared to the lot of classical bulk antigen.

The bulk antigen preparations were formulated as vaccine by adsorption onto aluminium hydroxide and without preservative.

Testing for in vitro potency using the Abbott AUSZYME ELISA kit and thiomersal containing SB Biologicals hepatitis B monovalent vaccine as standard showed that high in vitro potency values were obtained. The antigen content measured by this test was nearly double the stated value of 20 µg protein per ml.

An increased reactivity of vaccine prepared from thiomersal free antigen was also seen in an inhibition assay with RF1 monoclonal antibody for binding to fixed antigen. About half the quantity of thiomersal free vaccine was required to give 50% inhibition of RF1 binding to fixed antigen as compared to antigen purified by the previously used process and formulated without preservative.

This increased antigenicity of the thiomersal free vaccine with respect to RF1 is consistent with the results from the in vitro potency test (antigen content) and with the RF1 antibody tests performed on the bulk antigen preparations.

A mouse immunogenicity test was performed using priming and booster vaccinations two weeks apart and doses of 2 and 0.4 µg antigen. Mice were bled on day 28, 14 days after the booster. The sera were analysed for antibody titre and isotype composition. A clear antigen dose effect was observed for the two doses administered but there was no statistically significant difference in the response in terms of antibody titres (GMT) between thiomersal free and preservative free vaccines.

No substantial differences were observed in the isotype profiles.

What is claimed is:

1. A method for producing a stable, immunogenic hepatitis B vaccine without thiomersal suitable for human use, the method comprising:
   (a) expressing the hepatitis B surface antigen (HBsAg) as a recombinant protein in *Saccharomyces cerevisiae;*
   (b) processing the yeast cells to provide a crude antigen preparation;
   (c) subjecting the crude antigen preparation to gel permeation chromatography, wherein the elution buffer used in the gel permeation chromatography does not contain thiomersal, thereby producing an antigen-containing eluant;
   (d) subjecting the antigen-containing eluant from step (c) to ion exchange chromatography;
   (e) adding cysteine to the antigen-containing eluant obtained after step (d);
   (f) subjecting the preparation from step (e) to ultracentrifugation, thereby obtaining a purified HBsAg; and
   (g) combining the purified HBsAg with a pharmaceutically acceptable excipient to produce a stable, immunogenic hepatitis B vaccine suitable for human use;
   wherein the HBsAg is maintained in a soluble form through steps a to g, and wherein no thiomersal is added to the resulting vaccine.

2. A method according to claim 1, wherein the cysteine is added to a final concentration of between 1 and 10 mM.

3. A method according to claim 1, wherein the cysteine is added to a final concentration of about 2 mM.

4. A method according to claim 1, wherein the ultracentrifugation is cesium-chloride ultracentrifugation.

5. A method according to claim 1, which further comprises an ion-exchange chromatography step after gel permeation (c) and before ultracentrifugation (d).

6. A method according to claim 1, wherein the ion-exchange chromatography is anion-exchange chromatography.

* * * * *